United States Patent [19]

Jaehrling et al.

[11] Patent Number: 4,936,831
[45] Date of Patent: Jun. 26, 1990

[54] IMPLANTABLE MEDICATION DOSAGE DEVICE FOR INJECTION OF A LIQUID MEDICATION INTO A LIVING ORGANISM

[75] Inventors: Peter Jaehrling, Puschendorf; Eugen Schweikert, Bubenreuth, both of Fed. Rep. of Germany

[73] Assignee: Siemens Aktiengesellschaft, Berlin and Munich, Fed. Rep. of Germany

[21] Appl. No.: 377,135

[22] Filed: Jul. 10, 1989

[30] Foreign Application Priority Data

Aug. 22, 1988 [DE] Fed. Rep. of Germany ....... 3828442

[51] Int. Cl.⁵ .............................................. A61M 1/00
[52] U.S. Cl. ................................... 604/131; 604/190; 128/DIG. 12; 210/489
[58] Field of Search ................... 210/489, 445, 446; 128/DIG. 12, DIG. 13; 604/126, 151, 190, 118, 122, 123, 131

[56] References Cited

U.S. PATENT DOCUMENTS

| | | | |
|---|---|---|---|
| 4,159,954 | 7/1979 | Gangemi | 210/489 |
| 4,443,218 | 4/1984 | Decant, Jr. et al. | 604/67 |
| 4,479,874 | 10/1984 | Rosenberg et al. | 210/445 |
| 4,486,190 | 12/1984 | Reinicke | 604/67 |
| 4,604,090 | 8/1986 | Reinicke | 604/122 |
| 4,715,852 | 12/1987 | Reinicke et al. | 128/DIG. 12 |

Primary Examiner—John D. Yasko
Assistant Examiner—Anthony Gutowski
Attorney, Agent, or Firm—Hill, Van Santen, Steadman & Simpson

[57] ABSTRACT

A filter arrangement is inserted in a medication track of an implantable dosage device between a medication reservoir and the medication dosage pump, characterized by the arrangement being fashioned of at least two-ply membrane filter, whose first membrane is composed of non-woven polypropylene fiber-fleece oriented opposite the flow direction of the medication and the second membrane being arranged downstream of the first membrane and being composed of a polypropylene fabric.

8 Claims, 1 Drawing Sheet

4,936,831

IMPLANTABLE MEDICATION DOSAGE DEVICE FOR INJECTION OF A LIQUID MEDICATION INTO A LIVING ORGANISM

BACKGROUND OF THE INVENTION

The present invention is directed to an implantable medication dosage device having an arrangement for injection of a liquid medication into a living organism, said device comprising a medication track that is formed of a subcutaneous refilling septum connected by a line to a medication reservoir which, in turn, is connected by a second line to a remotely controllable medication dosage pump that has an outlet connected by a line to a catheter and the device further includes a filter arrangement for filtering liquid medication being disposed in the second line.

Specific functions of the components of the medication track of implantable medication dosage devices for liquid medication, particularly pumps, valves and catheters, are sensitive to the contamination of liquid medication, which contamination is in the form of solid particles that can appear in spherical shapes or in fiber-like shapes, as well. As a consequence of a slight displacement volume of such a system per work clock and of the hydraulic pump principle, narrow passages, whose clearances are not more than 10 µm at certain locations will occur in the medication track. Blockage or malfunction of the components and/or leakage of the overall system can, consequently, occur at such locations due to particles of this order of magnitude that are located in the stream of the medication. Over and above this, such particles can lead to an increase in the flow resistance and, thus, influence the pump performance in an inadmissible fashion.

In order to avoid such particle-dependent malfunctions of an implantable dosage means, U.S. Pat. No. 4,486,190, whose disclosure is incorporated by reference, discloses providing a filter arrangement which is inserted in a line between the subcutaneous paracentesis septum and the medication reservoir connected thereto by a hose line. This filter arrangement prevents solid particles present in the medication which is being added to the reservoir from proceeding into the medication reservoir. A filter arranged at this location, in fact, makes it possible to avoid manufacture-caused contaminations in the medication solution itself. Particles that occur in the medication reservoir, for example due to denaturing processes of the filled medication or due to contamination, however, are not removed by such a filter.

SUMMARY OF THE INVENTION

The object of the present invention is to construct a filter and arrange the filter so that the contamination present in the medication solution due to manufacture as well as contamination that may arise during the storing phase of the medication are eliminated before entry of the medication into the dosage pump without deteriorating the pump action, for instance due to excessive flow resistance.

These objects are achieved in an improvement in an implantable medication dosage device for the injection of a liquid medication into a living organism, said device comprising a medication track that is formed of a subcutaneous refilling septum which is connected by a filling hose to a medication reservoir, said medication reservoir being connected by a second hose to a controllable medication dosage pump which has an output connected by a line or hose to a catheter that supplies the medication conveyed by the medication dosage pump to the organism, said device further including a filter means for filtering liquid medication. The improvements are that the filter means is arranged in the medication track in a line which is between the medication reservoir and the medication dosage pump and that the filter means comprises at least a two-membrane filter whose first membrane is composed of a non-woven polypropylene fiber-fleece having orientation opposite to a flow direction of the medication and whose second membrane is arranged downstream of the first membrane and is made of a polypropylene fabric.

What is achieved with the improvement is that all particles contained in the medication solution, due to manufacturer or that where formed therein due to storage of the solution in the reservoir or that are brought into the reservoir, are eliminated immediately before the pump even and particles formed in the filter itself, due to, for instance, the separation of fibers of the filter, are intercepted.

The embodiment may include a second or additional filter arrangement either between the paracentesis septum and the medication reservoir or between the medication dosage pump and the catheter or at both positions.

Other advantages and features of the invention will be readily apparent from the following description of the preferred embodiments, the drawings and claims.

DESCRIPTION OF THE PREFERRED EMBODIMENTS

Figure 1:
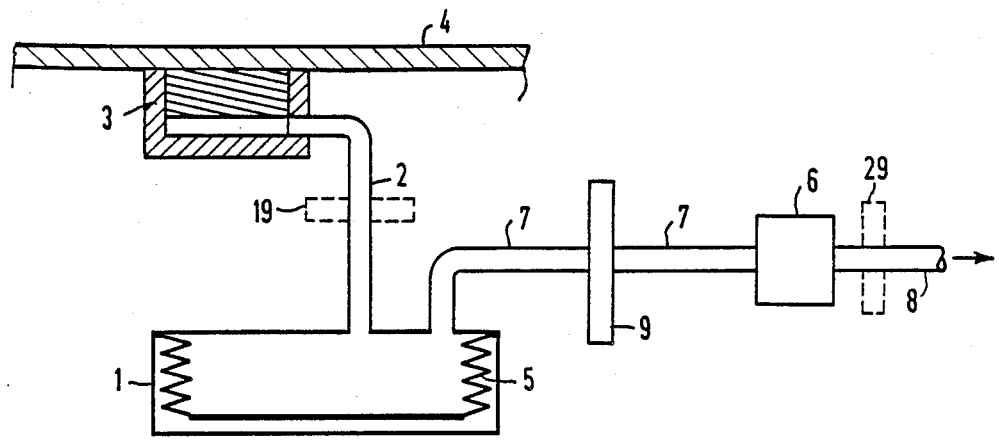
FIG. 1 is a diagrammatical view of an implantable medication dosage system in accordance with the present invention.
Figure 2:
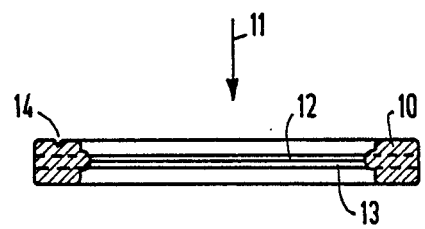
FIG. 2 is an enlarged cross sectional view of the filter arrangement of the system of FIG. 1.

The principles of the present invention are particularly useful when incorporated into a medication dosage system, which is shown in a schematic fashion in FIG. 1. The medication dosage system includes a reservoir 1 which has a membrane bellows reservoir 5. The reservoir 1 is connected by a filling hose or line 2 to a paracentesis septum 3 which is arranged under the skin for the living organism so that a liquid medication can be filled into the membrane bellows 5 of the medication reservoir 1 after it has been emptied by using a needle inserted into the septum 3 in a known manner. A medication dosage pump 6 draws a liquid medication from the membrane bellows reservoir 5 through a line or hose 7 in metered portions and conducts these portions to a line 8 extending to a catheter that transports the medication portions to a suitable location of the organism and injects them therein. The medication dosage pump 6 is remotely controlled in a known manner with means that are not illustrated and the individual medication portions can be fixed on the basis of variable criteria, as is known in the art. A filter arrangement 9, whose internal structure is shown in greater detail in FIG. 2, is inserted into the connecting hose or line 7.

What is hereby involved is that the filter 9 includes a housing containing a two-ply membrane filter having two membranes arranged one after the other in a flow direction, which is indicated by the arrow 11. The two membranes are secured in an annular holding frame 10. A first membrane 12 in the flow direction 11 is composed of a non-woven polypropylene fiber-fleece having a supporting fleece and an orientation opposite the flow direction. The flow-through openings have an area of about 1 cm$^2$. The density of the membrane is selected so that it has a retention rate of $\geq 5$ μm given a medication flow of a range of 50–120 milliliters per minute and a maximum pressure differential of 100 mbar. What is referred to as a bubble point, which is the pressure at which the first bubble passes through the membrane, will occur at a pressure of 10–20 mbar. The second membrane 13 is arranged to follow the first membrane in the direction of the arrow 11 and is composed of a fabric of polypropylene. This type of fabric leads to a pore width of about 25 μm and does not comprise any straight-line through pores.

Both filter membranes 12 and 13 are mounted in a frame 10 which is an injected molded polypropylene ring-shaped member to provide a peripherally tight arrangement. The annular holding frame 10 serves both as a holder as well as a seal relative to the surrounding housing of the filter arrangement 9. The holding frame 10 is also provided with a marking, such as 14, for the identification of the entry side of the medication stream.

Alternative to the positioning the filter arrangement, as illustrated in FIG. 1 and, in addition to the filter arrangement 9 of FIG. 1, a similar filter arrangement 19 can be placed between the septum 3 and the medication reservoir 1 on the line or hose 2 or the similar arrangement 29 can be placed on the discharge line 8 from the dosage pump 6 prior to reaching the catheter. Thus, the possibilities exist of a single arrangement 9, a combination of the arrangement 9 with the filter arrangement 19 on the hose 2, a combination of the filter 9 with a filter arrangement 29 on the output of the pump 6, or a combination of the filter arrangements 9, 19 and 29.

Although various minor modifications may be suggested by those versed in the art, it should be understood that we wish to embody within the scope of the patent granted hereon all such modifications as reasonably and properly come within the scope of our contribution to the art.

We claim:

1. In an implantable medication dosage device for injection of a liquid medication into a living organism, said device comprising a medication track being formed by a subcutaneous refilling septum connected by a hose to a medication reservoir, said medication reservoir being connected by a second hose to a remotely controllable dosage pump having an output hose connected to a catheter to supply the medication conveyed by the medication dosage pump to the organism, the improvements comprising a filter arrangement being arranged in the medication track on the second hose extending between the medication reservoir and the medication dosage pump, said filter arrangement being constructed of at least two membrane filters, with the first membrane filter being composed of a non-woven polypropylene fiber-fleece oriented opposite to a flow direction of the medication and the second membrane being arranged downstream of the first membrane and being composed of a fabric of polypropylene.

2. In an implantable medication dosage device according to claim 1, which further includes a second filter arrangement being disposed on the output hose extending between the medication dosage pump and the catheter, said second filter arrangement having the same structure as the first-mentioned filter arrangement.

3. In an implantable medication dosage device according to claim 2, wherein the first membrane has a retention rate of $\geq 5$ μm with an area of 1 cm$^2$, a medication flow of in a range of 50–120 milliliters per minute and a maximum pressure difference of 100 mbar, said second membrane of the filter device having a pore width of 25 μm and having no straight-line through pores.

4. In an implantable medication dosage device according to claim 2, which includes a third filter arrangement disposed on the hose extending between the septum and the reservoir, said third filter arrangement having the same structure as the first mentioned filter arrangement.

5. In an implantable medication dosage device according to claim 4, wherein the first member of each filter arrangement has a retention rate of $\geq 5$ μm given an area of about 1 cm$^2$, a medication flow of a range of 50–120 milliliters per minute and a maximum pressure difference of 100 mbar and wherein each of the second membranes has a pore width of 25 μm and has no straight-line through pores.

6. In an implantable medication dosage device according to claim 1, which includes a second filter arrangement identical to said first-mentioned filter arrangement being arranged on the hose extending between the septum and the medication reservoir.

7. In an implantable medication dosage device according to claim 6, wherein the first membrane of each of the filter arrangements has a retention rate of $\geq 5$ μm given an area of about 1 cm$^2$, a medication flow of a range of 50–120 milliliter per minute and a maximum pressure difference of 100 mbar, and each of the second membranes has a pore width of about 25 μm and has no straight-line pores.

8. In an implantable medication dosage device according to claim 1, wherein the first membrane has a retention rate of $\geq 5$ μm given an area of about 1 cm$^2$, a medication flow of in a range of 50–120 milliliters per minute and a maximum pressure difference of 100 mbar, and the second membrane has a pore width of 25 μm and has no straight-line through pores.

* * * * *